United States Patent
Komatsu et al.

(10) Patent No.: US 11,229,129 B2
(45) Date of Patent: Jan. 18, 2022

(54) HOUSING, ELECTRONIC DEVICE, METHOD FOR MANUFACTURING HOUSING, AND METHOD FOR MANUFACTURING ELECTRONIC DEVICE

(71) Applicant: KABUSHIKI KAISHA TOSHIBA, Tokyo (JP)

(72) Inventors: Izuru Komatsu, Yokohama (JP); Satoru Asagiri, Yokohama (JP)

(73) Assignee: KABUSHIKI KAISHA TOSHIBA, Tokyo (JP)

( * ) Notice: Subject to any disclaimer, the term of this patent is extended or adjusted under 35 U.S.C. 154(b) by 0 days.

(21) Appl. No.: 17/136,159

(22) Filed: Dec. 29, 2020

(65) Prior Publication Data
US 2021/0120684 A1  Apr. 22, 2021

Related U.S. Application Data

(63) Continuation of application No. PCT/JP2019/036138, filed on Sep. 13, 2019.

(51) Int. Cl.
*G06F 1/16* (2006.01)
*H05K 5/00* (2006.01)
(Continued)

(52) U.S. Cl.
CPC ........ *H05K 5/0204* (2013.01); *H05K 5/065* (2013.01)

(58) Field of Classification Search
CPC ...... H05K 5/0204; H05K 5/02; H05K 5/0208; H05K 5/0217; H05K 5/0221; H05K 5/065;
(Continued)

(56) References Cited

U.S. PATENT DOCUMENTS 8,561,795 B2 * 10/2013 Schott ................ A61B 5/151
206/439
8,808,202 B2 * 8/2014 Brancazio ............ A61B 10/02
600/583

(Continued)

FOREIGN PATENT DOCUMENTS

JP        8-322809 A    12/1996
JP    2008-237571 A    10/2008
(Continued)

OTHER PUBLICATIONS

International Search Report dated Nov. 26, 2019 in PCT/JP2019/036138 filed Sep. 13, 2019, citing documents AC and AT-AV therein, 2 pages.

*Primary Examiner* — Anthony M Haughton
(74) *Attorney, Agent, or Firm* — Oblon, McClelland, Maier & Neustadt, L.L.P.

(57) ABSTRACT

A housing according to the embodiment includes a lower surface part, an upper surface part, and a side surface part. The lower surface part includes a contact surface contacting an adherend. The upper surface part is separated in a vertical direction from the lower surface part with a first space interposed. The side surface part is provided around the first space and is connected to the upper surface part and the lower surface part. The upper surface part and the side surface part include a first material. The lower surface part includes a second material that is softer than the first material. A portion that includes the second material is exposed for at least a portion of the contact surface.

16 Claims, 11 Drawing Sheets

(51) Int. Cl.
*H05K 7/00* (2006.01)
*H05K 5/02* (2006.01)
*H05K 5/06* (2006.01)

(58) Field of Classification Search
CPC .......... H05K 5/06; H05K 5/064; H05K 5/062; H05K 5/061; H05K 5/066
See application file for complete search history.

(56) References Cited

U.S. PATENT DOCUMENTS

| | | | | |
|---|---|---|---|---|
| 8,821,412 | B2* | 9/2014 | Gonzalez-Zugasti | A61B 5/150099 600/583 |
| 9,033,898 | B2* | 5/2015 | Chickering, III | A61B 5/150389 600/573 |
| 9,041,541 | B2* | 5/2015 | Levinson | G16H 40/67 340/573.1 |
| 9,113,836 | B2* | 8/2015 | Bernstein | A61B 5/1438 |
| 9,295,417 | B2* | 3/2016 | Haghgooie | A61B 5/150099 |
| 10,543,310 | B2* | 1/2020 | Bernstein | A61M 37/0015 |
| 10,638,963 | B2* | 5/2020 | Beyerlein | B01L 3/5023 |
| 2008/0243026 | A1 | 10/2008 | Tsuji | |
| 2011/0105952 | A1 | 5/2011 | Bernstein et al. | |
| 2020/0214126 | A1 | 7/2020 | Nakashima et al. | |

FOREIGN PATENT DOCUMENTS

| | | |
|---|---|---|
| JP | 2008-291232 A | 12/2008 |
| JP | 2009-45789 A | 3/2009 |
| JP | 2015-128562 A | 7/2015 |
| JP | 6078565 B2 | 2/2017 |
| JP | 2017-126612 A | 7/2017 |
| JP | 2017-169790 A | 9/2017 |
| JP | 2019-59151 A | 4/2019 |

* cited by examiner

FIG. 11

HOUSING, ELECTRONIC DEVICE, METHOD FOR MANUFACTURING HOUSING, AND METHOD FOR MANUFACTURING ELECTRONIC DEVICE

CROSS-REFERENCE TO RELATED APPLICATIONS

This is a continuation application of International Patent Application PCT/JP2019/036138, filed on Sep. 13, 2019. This application also claims priority to Japanese Patent Application No. 2019-057322, filed on Mar. 25, 2019. The entire contents of which are incorporated herein by reference.

FIELD

Embodiments described herein relate generally to a housing, an electronic device, a method for manufacturing the housing, and a method for manufacturing the electronic device.

BACKGROUND

An electronic device includes a housing, and an electronic component provided inside the housing. The electronic device is used by being adhered to a human, an object, etc. It is desirable for the housing of the electronic device to be easy to adhere and not to peel off easily.

DETAILED DESCRIPTION

A housing according to the embodiment includes a lower surface part, an upper surface part, and a side surface part. The lower surface part includes a contact surface contacting an adherend. The upper surface part is separated in a vertical direction from the lower surface part with a first space interposed. The side surface part is provided around the first space and is connected to the upper surface part and the lower surface part. The upper surface part and the side surface part include a first material. The lower surface part includes a second material. The second material is a resin material that is softer than the first material. A portion that includes the second material is exposed for at least a portion of the contact surface.

Various embodiments are described below with reference to the accompanying drawings.

The drawings are schematic and conceptual; and the relationships between the thickness and width of portions, the proportions of sizes among portions, etc., are not necessarily the same as the actual values. The dimensions and proportions may be illustrated differently among drawings, even for identical portions.

In the specification and drawings, components similar to those described previously in an antecedent drawing are marked with like reference numerals, and a detailed description is omitted as appropriate.

Figure 1:
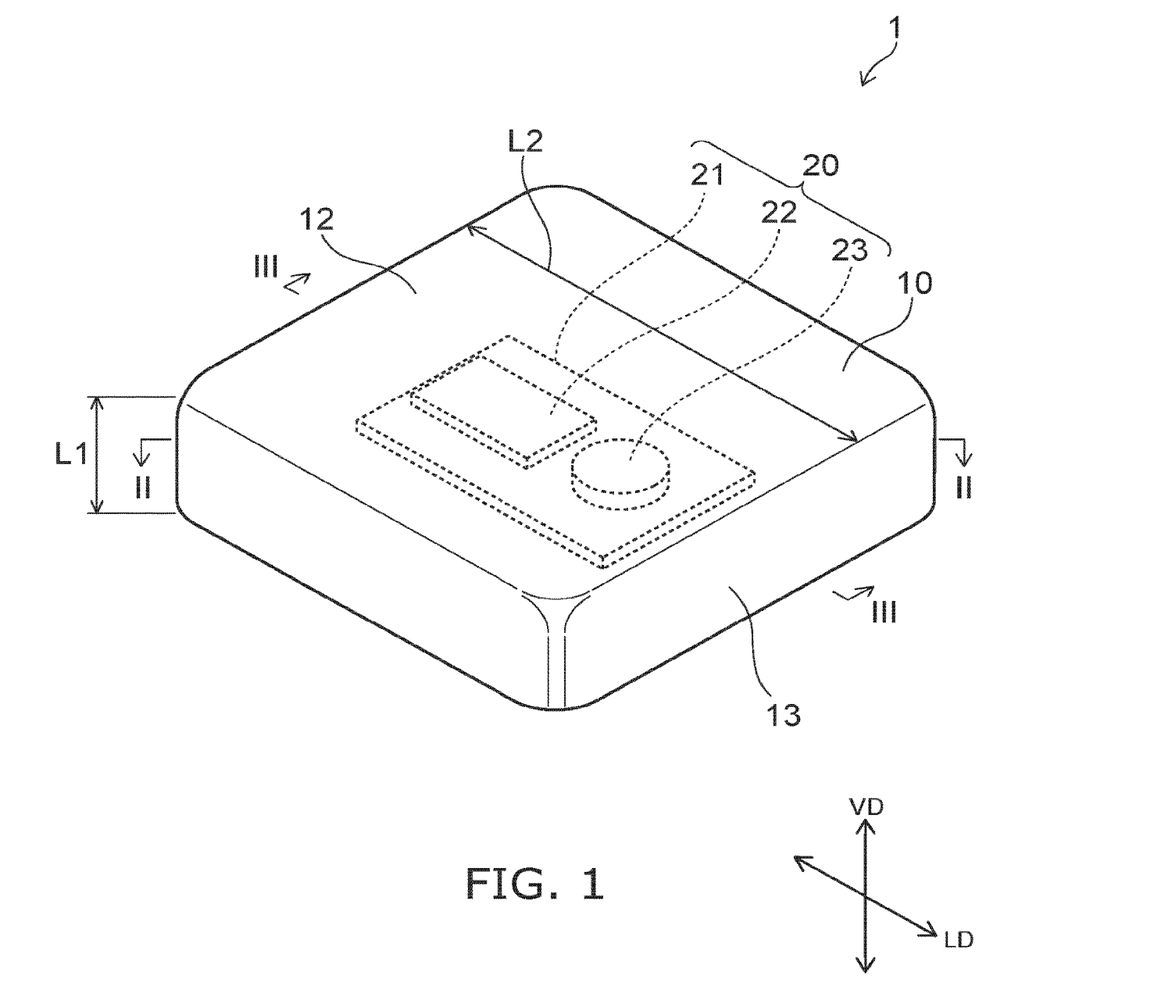
FIG. 1 is a perspective view illustrating an electronic device according to an embodiment.

FIG. 1 is a perspective view illustrating an electronic device according to an embodiment.

Figure 2:
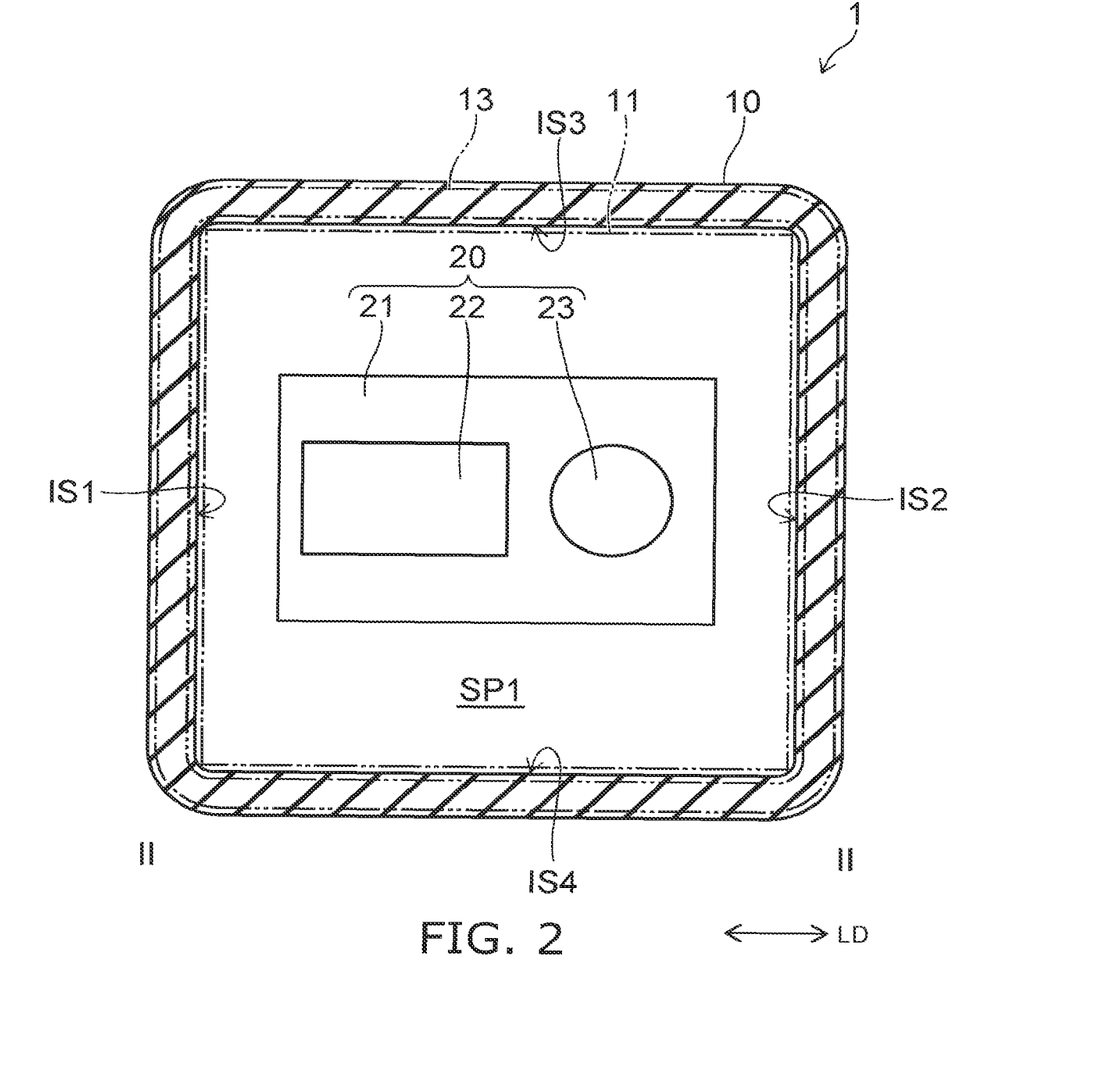
FIG. 2 is a II-II cross-sectional view of FIG. 1.

FIG. 2 is a II-II cross-sectional view of FIG. 1.

Figure 3:
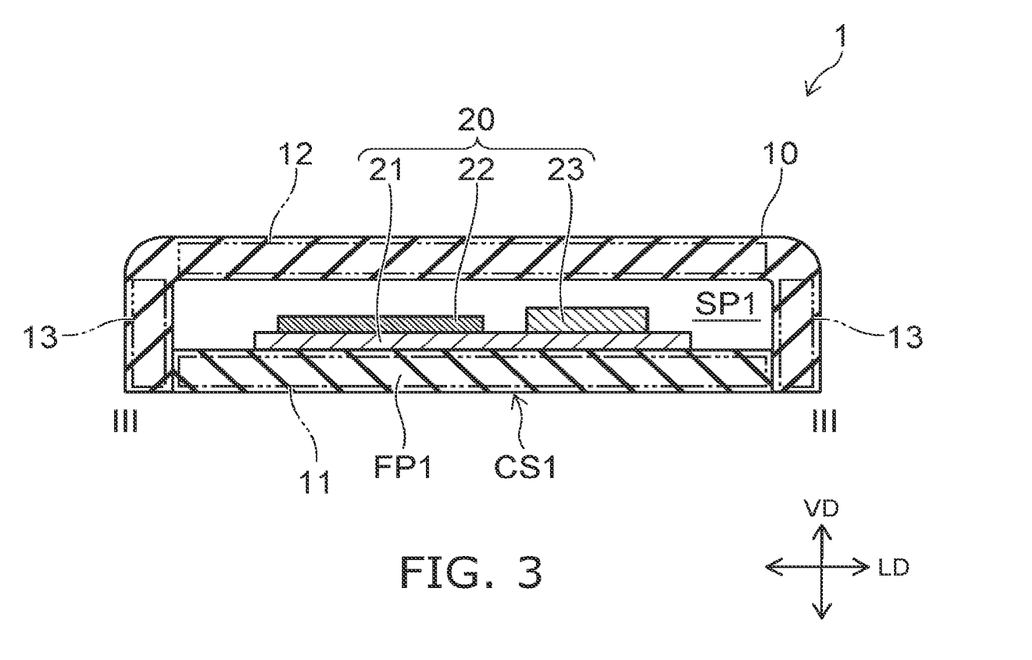
FIG. 3 is a III-III cross-sectional view of FIG. 1.

FIG. 3 is a III-III cross-sectional view of FIG. 1.

As illustrated in FIGS. 1 to 3, the electronic device 1 according to the embodiment includes a housing 10 and an electronic component 20.

The housing 10 is box-shaped, and a first space SP1 is formed inside the housing 10. The electronic component 20 is provided in the first space SP1. For example, the first space SP1 is airtight with respect to the external space. Therefore, the electronic device 1 is waterproof for the electronic component 20.

Specifically, as illustrated in FIGS. 1 to 3, the housing 10 includes a lower surface part 11, an upper surface part 12, and a side surface part 13. The electronic device 1 can be adhered to an object, a human, etc. The lower surface part 11 includes a contact surface CS1 that contacts an adherend such as an object, a human, etc. For example, the electronic component 20 is placed or bonded on the lower surface part 11. The upper surface part 12 is separated from the lower surface part 11 in a direction crossing the contact surface CS1 with the first space SP1 interposed.

Here, "up" and "down" are used for convenience of description. "Up" and "down" are based on the positional relationship between the lower surface part 11 and the upper surface part 12 and are independent of the direction of gravity. For example, as illustrated in FIGS. 1 to 3, a vertical direction VD is along a direction perpendicular to the contact surface CS1.

The side surface part 13 is provided around the first space SP1. The end portion in the vertical direction VD of the side surface part 13 is connected to the lower surface part 11 and the upper surface part 12.

In the example illustrated in FIGS. 1 to 3, the side surface part 13 includes inner surfaces IS1 to IS4. The inner surfaces IS1 and IS2 face each other. The inner surfaces IS3 and IS4 face each other. Therefore, as illustrated in FIG. 2, the housing 10 is rectangular when viewed in plan. The number of surfaces of the side surface part 13 is not limited to the example. For example, when viewed in plan, the housing 10 may be triangular or may be polygonal with five or more vertices. Or, a curved side surface part 13 may be provided, and the housing 10 may be circular or elliptical when viewed in plan.

A length L1 of the housing 10 in the vertical direction VD is less than a length L2 of the housing 10 in a lateral direction LD perpendicular to the vertical direction VD. The thicknesses of the lower surface part 11, the upper surface part 12, and the side surface part 13 may be equal to each other or may be different from each other.

The upper surface part 12 and the side surface part 13 include a first material. At least a portion of the lower surface part 11 includes a second material. The second material is a resin material that is softer than the first material. In other words, the hardness of the second material is less than the hardness of the first material. Therefore, the second material deforms more easily than the first material and is adhered to the adherend more easily than the first material. In other words, at least a portion of the lower surface part 11 is softer than the upper surface part 12 and the side surface part 13 and is adhered to the adherend more easily than the upper surface part 12 and the side surface part 13.

A portion that includes the second material is exposed at the contact surface CS1. Therefore, the electronic device 1 can be adhered to the adherend by causing the portion including the second material to contact the adherend.

The first material is, for example, at least one selected from the group consisting of a resin material, a metal material, and an inorganic material. The resin material (a first resin material) includes at least one of silicone, urethane, epoxy, Teflon (registered trademark), polycarbonate, nylon, or acrylic. The metal material includes at least one of aluminum, an aluminum alloy, copper, a copper alloy, iron, or an iron alloy. The inorganic material includes at least one of glass or silicon. The second material includes, for example, at least one of a silicone gel, a urethane gel, or an acrylic gel.

For example, the upper surface part 12 and the side surface part 13 are formed from the first material. The upper surface part 12 and the side surface part 13 are formed to have a continuous body. In other words, the upper surface part 12 and the side surface part 13 are seamless without a joint or the like due to bonding.

For example, the lower surface part 11 is formed from a soft part FP1 made of the second material. The lower surface part 11 is bonded to the side surface part 13. The soft part FP1 is exposed at the contact surface CS1. For example, the lower surface part 11 and the side surface part 13 are bonded by an adhesive. Or, the lower surface part 11 and the side surface part 13 may be bonded by a covalent bond between the second material included in the lower surface part 11 and the first material included in the side surface part 13 at the bonding surface between the lower surface part 11 and the side surface part 13.

The electronic component 20 includes, for example, a substrate 21, and a chip 22 and a battery 23 that are mounted to the substrate 21. For example, the battery 23 is rechargeable, and wireless power supply to the battery 23 can be performed from a power supply device provided outside the housing 10.

Figure 4A:
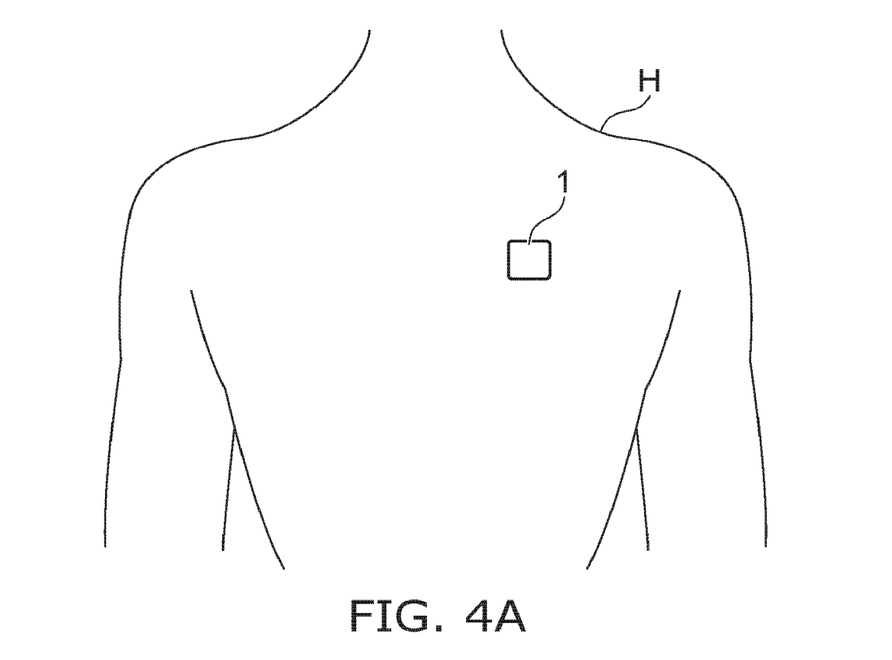
FIGS. 4A and 4B are schematic views illustrating applications of the electronic device 1 according to the embodiment.
Figure 4B:
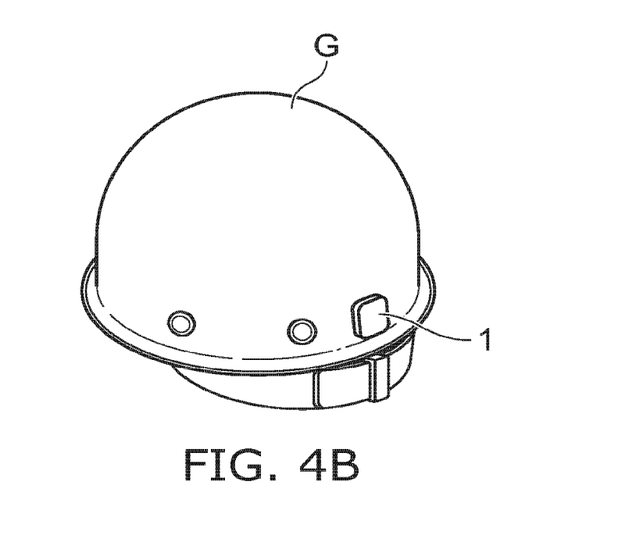

FIGS. 4A and 4B are schematic views illustrating applications of the electronic device 1 according to the embodiment.

For example, the electronic component 20 can acquire biological information. As illustrated in FIG. 4A, the electronic device 1 is adhered to a portion of a human body H and acquires biological information of the human. The acquired biological information includes, for example, at least one of an electrocardiographic potential, a pulse wave, blood pressure, skin temperature, water content, myoelectricity, or a brain wave.

The electronic component 20 may be capable of acquiring at least one of operation information, environmental information, or position information. The operation information includes, for example, at least one of an acceleration or an angular velocity. The environmental information includes at least one of air pressure, temperature, or ultraviolet amount.

For example, as illustrated in FIG. 4B, the electronic device 1 is adhered to an object G and acquires information of the object G indicating the position. For example, when adhered to an object worn by a human, the electronic device 1 can acquire position information of the human. When adhered to an object that is transferred, the electronic device 1 can acquire position information of the transfer object.

For example, the electronic device 1 acquires logistics information relating to components and/or products inside a plant. The logistics information includes at least one of position information of the components and/or the products inside the plant or movement information of the components and/or the products inside the plant. The electronic device 1 may acquire operation information such as vibrations, temperature, a range of movement, etc., relating to a designated machine. The electronic device 1 may acquire behavior information relating to a designated person such as the position, the movement range, the position, etc., of the person. The electronic device 1 may acquire information of movable positions of the head, body, limbs, fingers, etc., of a human body.

Figure 5A:
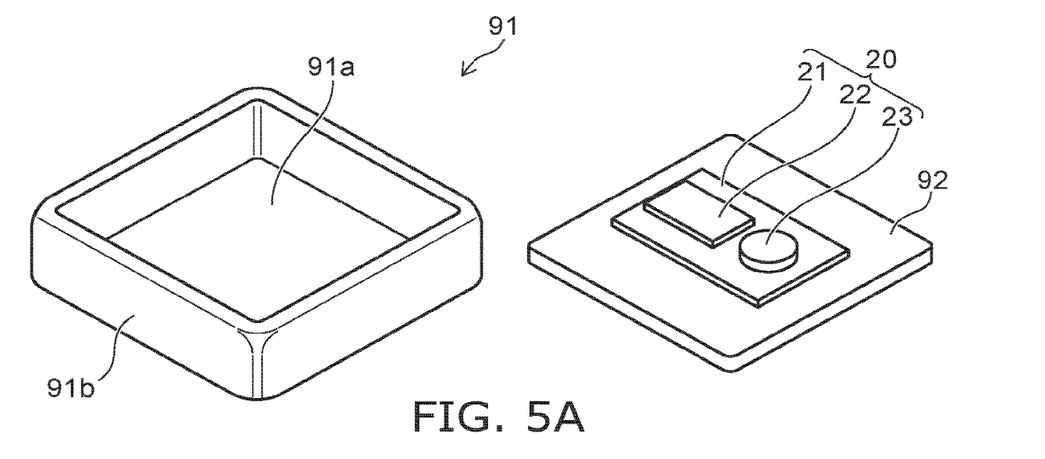
FIGS. 5A and 5B are process drawings illustrating a method for manufacturing the electronic device according to the embodiment.
Figure 5B:
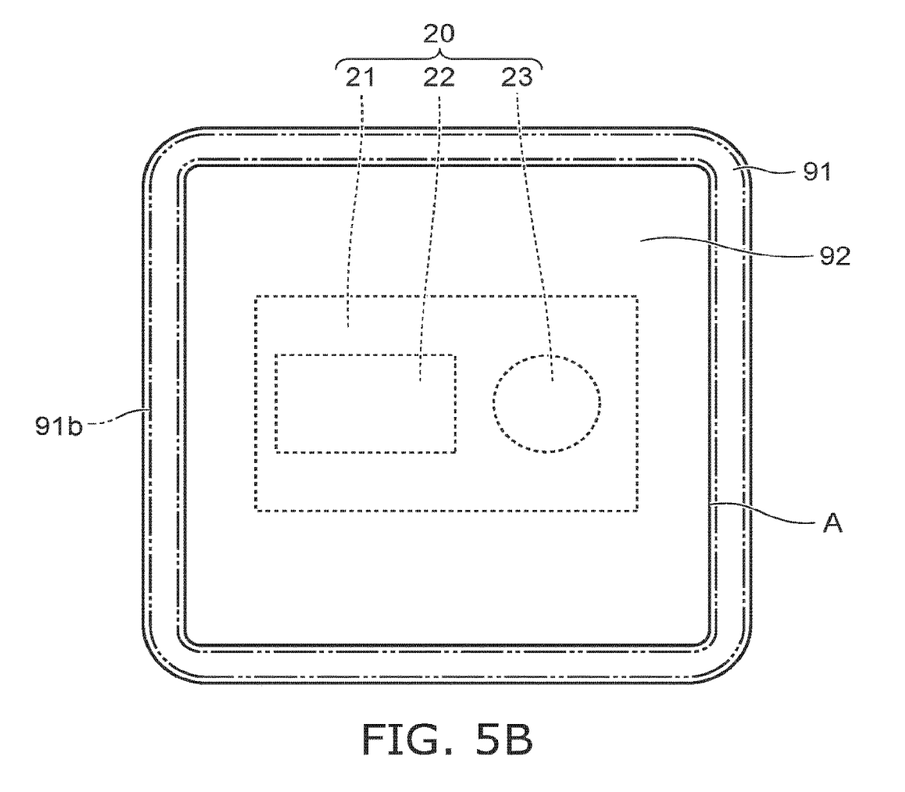

FIGS. 5A and 5B are process drawings illustrating a method for manufacturing the electronic device according to the embodiment.

A first member 91 and a second member 92 are prepared as illustrated in FIG. 5A. The first member 91 includes the first material. The second member 92 includes the second material. The first member 91 includes a first housing part 91a and a second housing part 91b. The first housing part 91a has a flat shape. The second housing part 91b is connected to the outer perimeter of the first housing part 91a. The first member 91 includes the first space SP1 surrounded with the first and second housing parts 91a and 91b. The second member 92 has a flat shape similar to that of the first housing part 91a. The electronic component 20 is provided on the second member 92.

The first member 91 may be made by bonding separate first and second housing parts 91a and 91b, or the first housing part 91a and the second housing part 91b may be formed to have a continuous body. The method for making the first member 91 is modifiable as appropriate as long as the first housing part 91a and the second housing part 91b are connected. However, to improve the strength of the first member 91, it is desirable for the first housing part 91a and the second housing part 91b to be formed to have a continuous body. In other words, it is desirable for the first housing part 91a and the second housing part 91b to be seamless without a joint or the like due to bonding.

FIG. 5B illustrates the appearance of the first and second members 91 and 92 when viewed from below. As illustrated in FIG. 5B, the second housing part 91b of the first member 91 is bonded at a bonding surface A positioned at the outer perimeter of the second member 92. For example, when bonding the first member 91 and the second member 92, the bonding location of the first member 91 and the bonding location of the second member 92 are activated by a method such as plasma modification, ultraviolet light irradiation, exposure to corona discharge, etc. By causing the activated bonding locations to contact each other, the activated molecules form covalent bonds with each other, and the first member 91 and the second member 92 are bonded. Or, an adhesive may be used to bond the first member 91 and the second member 92. Thus, the electronic device illustrated in FIGS. 1 to 3 is manufactured.

Figure 6:
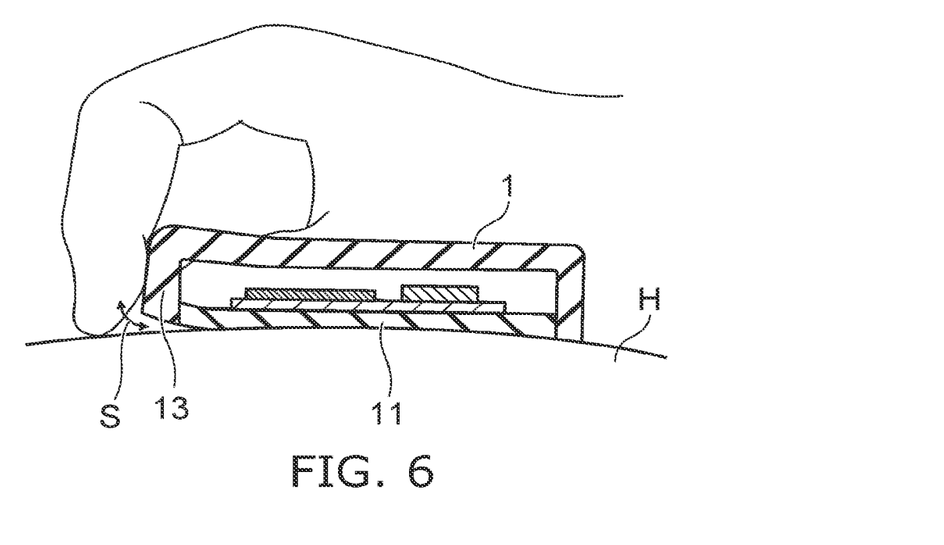
FIG. 6 is a cross-sectional view illustrating the electronic device according to the embodiment.

FIG. 6 is a cross-sectional view illustrating the electronic device according to the embodiment.

Figure 7A:
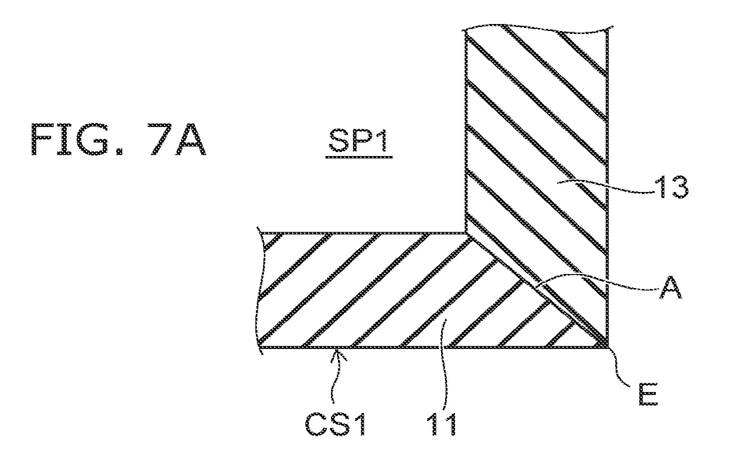
FIGS. 7A to 7C are enlarged cross-sectional views of portions of the electronic device according to the embodiment.
Figure 7B:
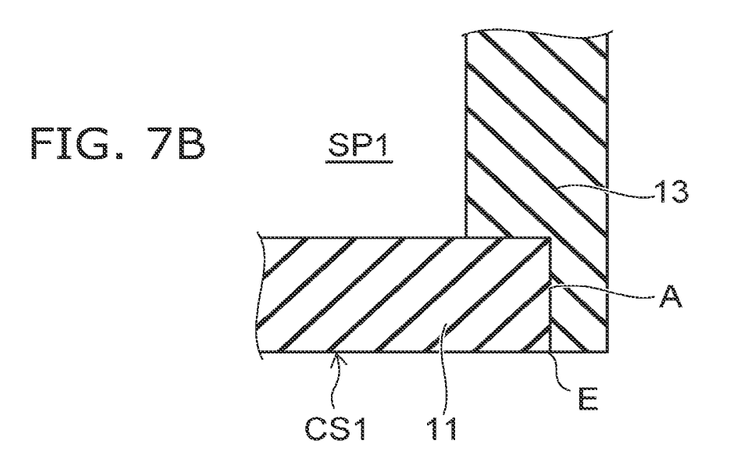
Figure 7C:
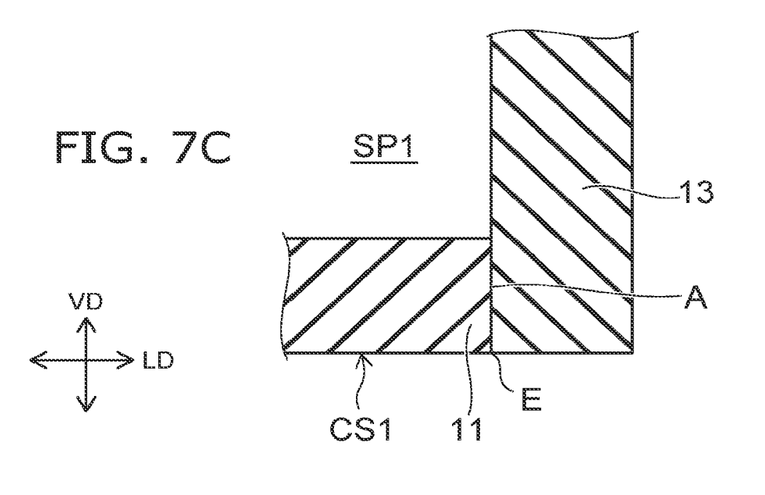

FIGS. 7A to 7C are enlarged cross-sectional views of portions of the electronic device according to the embodiment.

Figure 8:
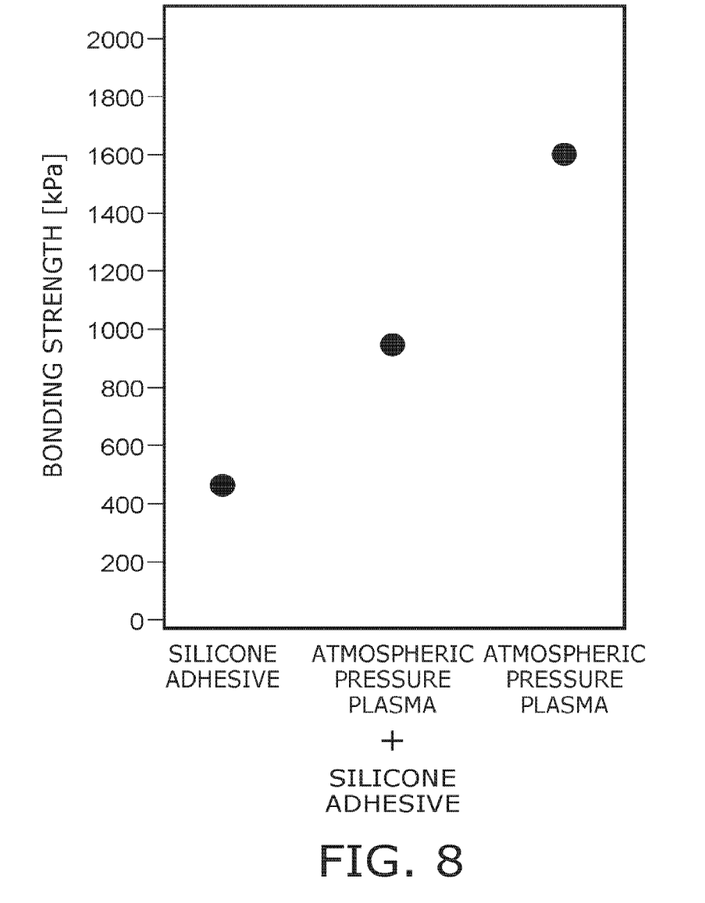
FIG. 8 is an experiment result illustrating a characteristic relating to the housing.

FIG. 8 is an experiment result illustrating a characteristic relating to the housing.

Effects of the embodiment will now be described with reference to FIGS. 6 to 8. In the housing 10 according to the embodiment, at least a portion of the lower surface part 11 is softer and more easily-deformable than the upper surface part 12 and the side surface part 13. Therefore, as illustrated in FIGS. 4A and 4B, the lower surface part 11 can deform along the shape of the surface of the adherend even when the surface of the adherend is curved or the surface has an unevenness. The contact area between the lower surface part 11 and the adherend can be increased thereby, and the electronic device 1 does not easily peel off from the adherend.

As a reference example, there is a method in which an adhesive sheet is used to adhere a housing including an electronic device to an adherend. In this method, the housing is adhered to a human body, an object, etc., via the sheet. However, in this method, wrinkles easily occur in the sheet when the housing is adhered, and the housing easily peels off from the adherend. When wrinkles occur in the sheet, it is necessary to use another new sheet, and the cost increases.

In the housing 10 according to the embodiment, the lower surface part 11 is bonded to the upper surface part 12 and the side surface part 13. Therefore, the occurrence of wrinkles in the contact surface CS1 adhered to the adherend can be suppressed even when the electronic device 1 is adhered to the adherend or detached from the adherend. When dirt adheres to the contact surface CS1, the strength (the adhesive force) of the adhesion to the adherend decreases. If, however, the portion that is adhered to the adherend is formed from a resin material, the contact surface CS1 can be washed with water, etc., even when dirt is adhered to the contact surface CS1. The adhesive force to the adherend can be recovered by washing the contact surface CS1.

When the electronic device 1 is detached from the adherend, the user hooks a finger on the side surface part 13 and/or pinches the side surface part 13 with fingers and applies a force to the housing 10. FIG. 6 illustrates the appearance when the electronic device 1 that is adhered to the human body H is detached by a finger. At this time, as illustrated in FIG. 6, a large tensile stress S occurs in the lower surface part 11 and the side surface part 13, and a force is transmitted from the side surface part 13 to the lower surface part 11. The lower surface part 11 is peeled from the adherend due to the force transmitted from the side surface part 13 to the lower surface part 11.

If the side surface part 13 includes the soft second material, the force is not easily transmitted from the side surface part 13 to the lower surface part 11, and it is difficult to peel the lower surface part 11 from the adherend. Because the second material is soft, there is a possibility that the second material may tear if a large stress is applied. By the side surface part 13 including the first material and the lower surface part 11 including the second material, the lower surface part 11 can easily be peeled from the adherend, and the damage of the housing 10 can be suppressed. The stickiness of the side surface part 13 that is touched by the user can be suppressed, and the user can comfortably use the electronic device 1.

When the lower surface part 11 is formed from the second material, it is desirable for at least a portion of the lower surface part 11 to overlap the side surface part 13 in the lateral direction LD as illustrated in FIGS. 7A to 7C. It is desirable for the length in the lateral direction LD of the lower surface part 11 to be not more than the length in the lateral direction LD of the housing 10. According to this configuration, the force is more easily transmitted from the side surface part 13 to the lower surface part 11. The force that is applied to the lower surface part 11 can be reduced, and the damage of the housing 10 can be further suppressed.

More desirably, as illustrated in FIGS. 7B and 7C, an edge portion E of the bonding surface A between the lower surface part 11 and the side surface part 13 is positioned at the contact surface CS1. According to this configuration, the force that is applied to the lower surface part 11 and the bonding surface A can be reduced, and the peeling-off of the bonding surface A and the tearing of the lower surface part 11 can be suppressed.

It is desirable for the bonding strength between the lower surface part 11 and the side surface part 13 to be greater than the tensile rupture strength of the lower surface part 11. When at least a portion of the lower surface part 11 overlaps the side surface part 13 in the lateral direction LD as described above, compared to the lower surface part 11, a larger force is applied to the bonding surface between the lower surface part 11 and the side surface part 13. When the bonding strength between the lower surface part 11 and the side surface part 13 is greater than the tensile rupture strength of the lower surface part 11, the occurrence of cracks and peeling-off at the bonding surface A when the force is applied to the housing 10 can be suppressed.

Characteristics of the first material will now be described.

The hardness of the upper surface part 12 and the side surface part 13 can be increased when the first material includes at least one of a metal material, an inorganic material, or a hard resin material. In other words, the upper surface part 12 and the side surface part 13 deform less easily. When the upper surface part 12 and the side surface part 13 deform less easily, the deformation of the housing 10 can be suppressed even when a force is applied to the housing 10 from above. Therefore, the damage of the housing 10 can be suppressed, and the electronic component 20 inside the housing 10 can be protected.

Here, the hard resin material refers to a Rockwell hardness not less than R50 or a durometer hardness not less than D50. The Rockwell hardness is measured using a test method standardized in JIS K 7202-2. JIS K 7202-2 corresponds to ISO 2039. The durometer hardness is a value measured by a type-D durometer conforming to JIS K 6253 using a method standardized in JIS K 6253-3. JIS K 6253-3 corresponds to ISO 7619.

Or, the first material may be a relatively soft resin material. For example, the hardness of the first material is not less than A10 and not more than A70. The hardness is a value measured by a type-A durometer conforming to JIS K 6253 using a method standardized in JIS K 6253-3. When the first material is a resin material having a hardness not less than A10 but less than A70, the hardness of the upper surface part 12 and the side surface part 13 can be small compared to when the first material is a metal material or an inorganic material. In other words, the upper surface part 12 and the side surface part 13 deform more easily. When the upper surface part 12 and the side surface part 13 easily deform, for example, the force that occurs in the lower surface part 11 can be reduced when the electronic device 1 is adhered to the adherend or detached from the adherend. Therefore, the tearing of the lower surface part 11 can be suppressed.

On the other hand, when the hardness of the first material is less than A10, the housing 10 deforms too easily. Therefore, there is a possibility that it may be difficult to hold the housing 10 or detach the adhered electronic device 1. When the hardness of the first material is greater than A70, there is a possibility that the upper surface part 12 and the side surface part 13 may not deform easily and the adhesive force may be weak when the housing 10 is adhered to a curved adherend. Accordingly, it is desirable for the hardness of the first material to be not less than A10 and not more than A70.

It is desirable for the penetration of the second material to be not less than 20 and not more than 40. The penetration is a value measured using a ¼ circular cone in a method standardized in JIS K 2220. JIS K 2220 corresponds to ISO 2137. In the application, a resin material that has a penetration measured by this method that is not less than 20 and not more than 40 is called a "gel".

When the penetration of the second material is less than 20, the deformation of the lower surface part 11 including the second material becomes small. Therefore, the contact area between the lower surface part 11 and the adherend may become small according to the surface shape of the adherend. When the penetration of the second material is greater than 40, handling is difficult because the lower surface part 11 greatly deforms due to the electronic component 20 and its own weight. The lower surface part 11 tears more easily. Accordingly, it is desirable for the penetration of the second material to be not less than 20 and not more than 40.

It is desirable for the elongation at breakage of the portion of the lower surface part 11 including the second material to be not less than 100%. By setting the elongation at break to be large, the portion that includes the second material is more difficult to damage when detaching the electronic device 1.

It is desirable for the first material to be a resin material. For example, the first material is silicone. For example, the second material is a silicone gel having a lower crosslink density than silicone, which is the first material. Thus, the first material and the second material may be the same type of resin material as long as the softness (e.g., the crosslink density) is different.

It is desirable for the lower surface part 11 and the side surface part 13 to be formed to have a continuous body by a covalent bond. In other words, when bonding the first member 91 and the second member 92 illustrated in FIG. 5A, it is desirable to bond by activating the bonding location of the first member 91 and the bonding location of the second member 92 and by causing the activated bonding locations to contact each other.

FIG. 8 shows test results when two resin members are bonded to each other. In the test, two resin members that are made of the first material are bonded to each other by an adhesive, plasma modification, or both an adhesive and plasma modification. In FIG. 8, the vertical axis is the bonding strength when bonded by each bonding method. In the test, the two resin members after bonding were pulled in mutually-opposite directions at a speed of 10 mm/min, and the strength when breakage occurred was measured as the bonding strength. FIG. 8 illustrates the average value of six measurements of the strength for the members bonded by an adhesive, plasma modification, and both an adhesive and plasma modification.

When bonding using both an adhesive and plasma modification, first, plasma modification of the bonding location of the first member 91 and the bonding location of the second member 92 was performed. Subsequently, an adhesive was coated onto the bonding locations, and the first member 91 and the second member 92 were bonded. KE941U made by Shin-Etsu Chemical Co., Ltd. was used as the resin members. A silicone adhesive (KE-4908-T) made by Shin-Etsu Chemical Co., Ltd. was used as the adhesive.

From FIG. 8, it can be seen that the bonding strength when the resin members were bonded to each other using plasma modification was greater than the bonding strength when the resin members were bonded to each other by only the adhesive. By forming the lower surface part 11 and the side surface part 13 to have a continuous body by a covalent bond, the damage when a force is applied to the housing 10 can be further suppressed. It can be seen that the bonding strength when the resin members are bonded to each other using only plasma modification is greater than the bonding strength when the resin members are bonded to each other using both an adhesive and plasma modification.

Other than plasma modification, the first member 91 and the second member 92 can be formed to have a continuous body by a covalent bond by using ultraviolet light or a corona discharge when bonding the first member 91 and the second member 92. However, when ultraviolet light or a corona discharge is used, a large amount of energy is applied not only to the surface of the member but also inside the member. There is a possibility that the main chains of resin material inside the member may be cut thereby, and the member may be altered. It is desirable to use plasma modification to more securely bond the first member 91 and the second member 92 while suppressing the change of the characteristics of the first and second members 91 and 92.

For example, plasma modification can be performed by the following procedure and conditions.

An atmospheric plasma generator DFMJ01 made by Plasma-Factory is used. Nitrogen gas is used for the plasma generation. The flow rate of the nitrogen gas is set to 10 L/min. The plasma generation nozzle is separated from the first member 91 or the second member 92 by 10 mm. The nozzle irradiates plasma on the bonding location while moving over the bonding location at a speed of 9 mm/s. The first member 91 and the second member 92 are bonded quickly after plasma irradiation, and are heated inside an oven for 1 hour at 110° C.

Figure 9A:
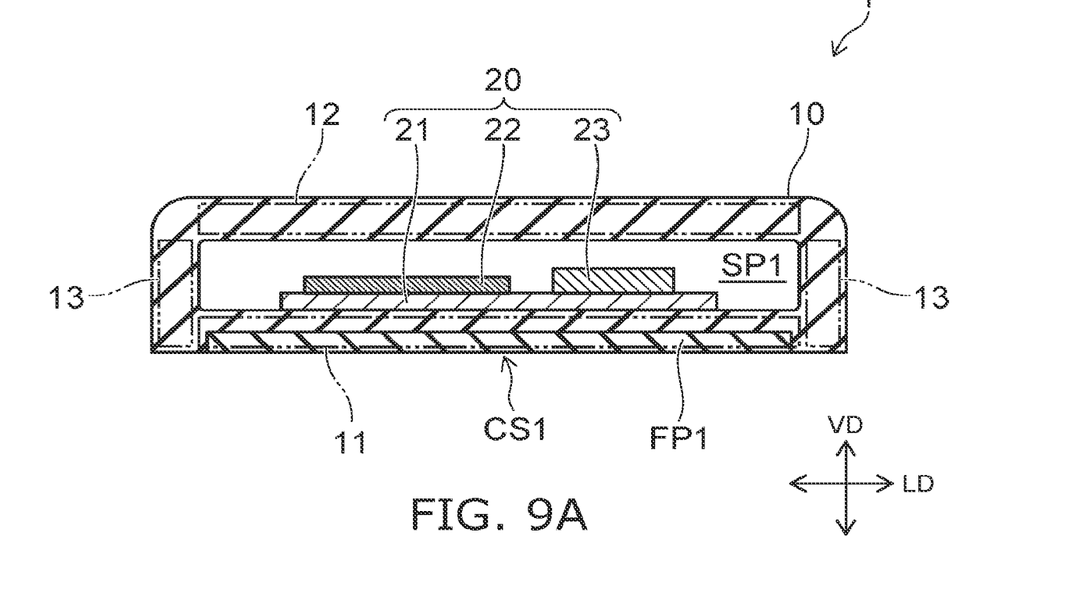
FIGS. 9A and 9B are cross-sectional views illustrating the electronic device according to the embodiment.
Figure 9B:
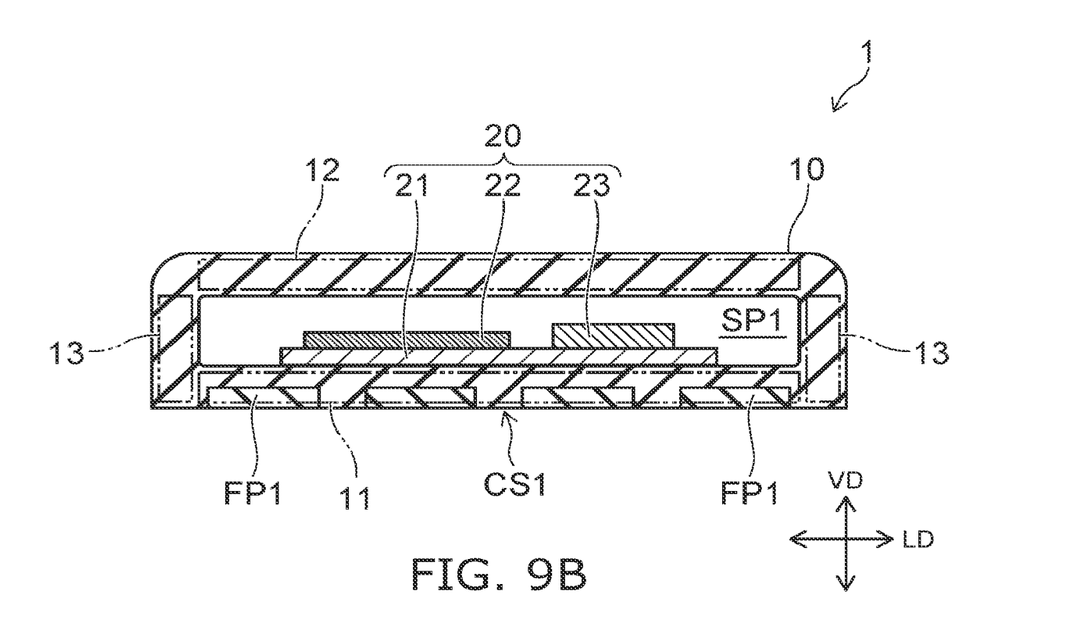

FIGS. 9A and 9B are cross-sectional views illustrating the electronic device according to the embodiment.

A portion of the lower surface part 11 may include the first material, and another portion of the lower surface part 11 may include the second material. For example, as illustrated in FIG. 9A, the portion of the lower surface part 11 facing the first space SP1 may include the first material, and the soft part FP1 of the lower surface part 11 that includes the second material may be provided at the contact surface CS1. As illustrated in FIG. 9B, multiple soft parts FP1 that include the second material and are separated from each other may be provided at the contact surface CS1.

(Modification)

Figure 10:
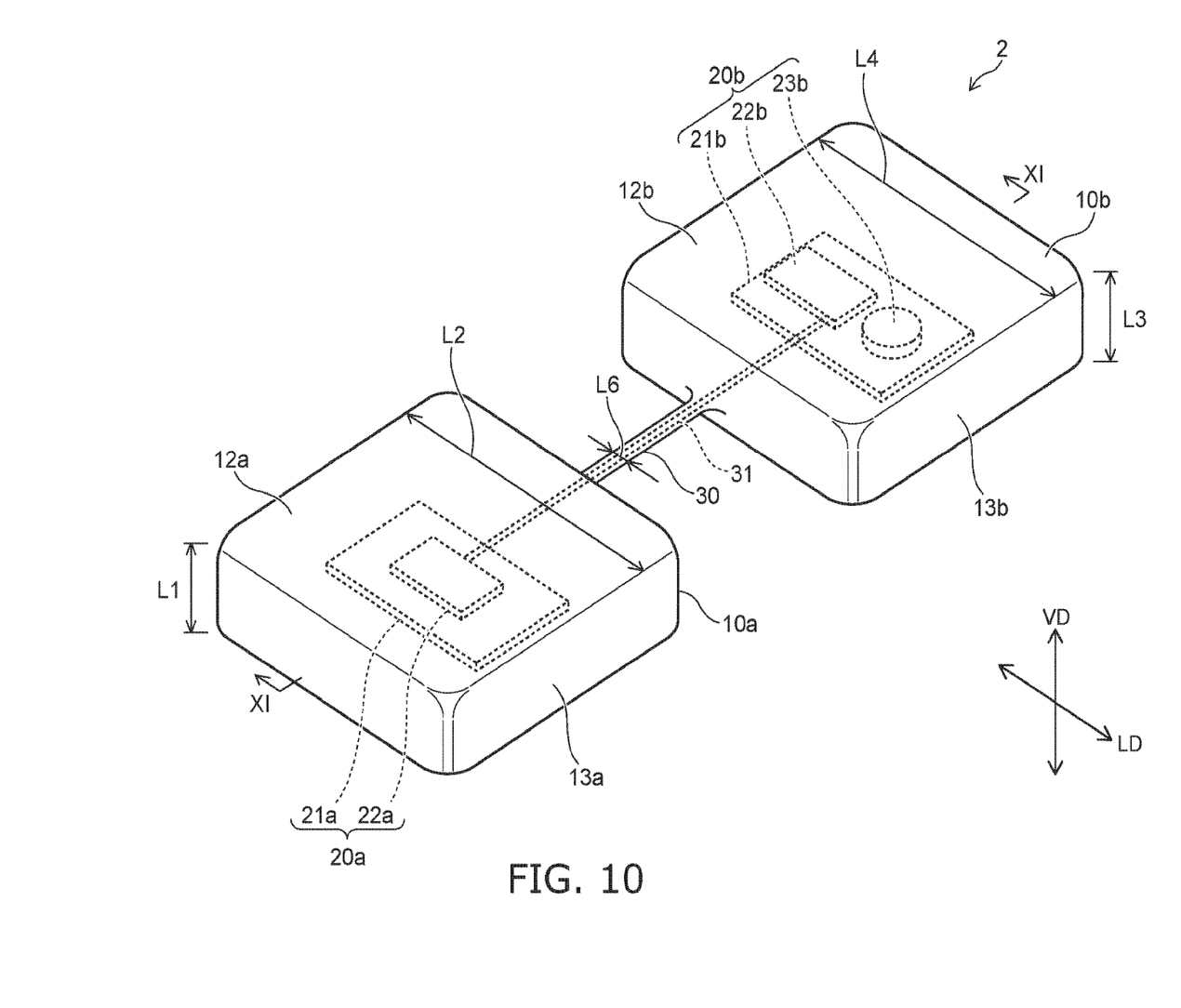
FIG. 10 is a perspective view illustrating an electronic device according to a modification of the embodiment.

FIG. 10 is a perspective view illustrating an electronic device according to a modification of the embodiment.

Figure 11:
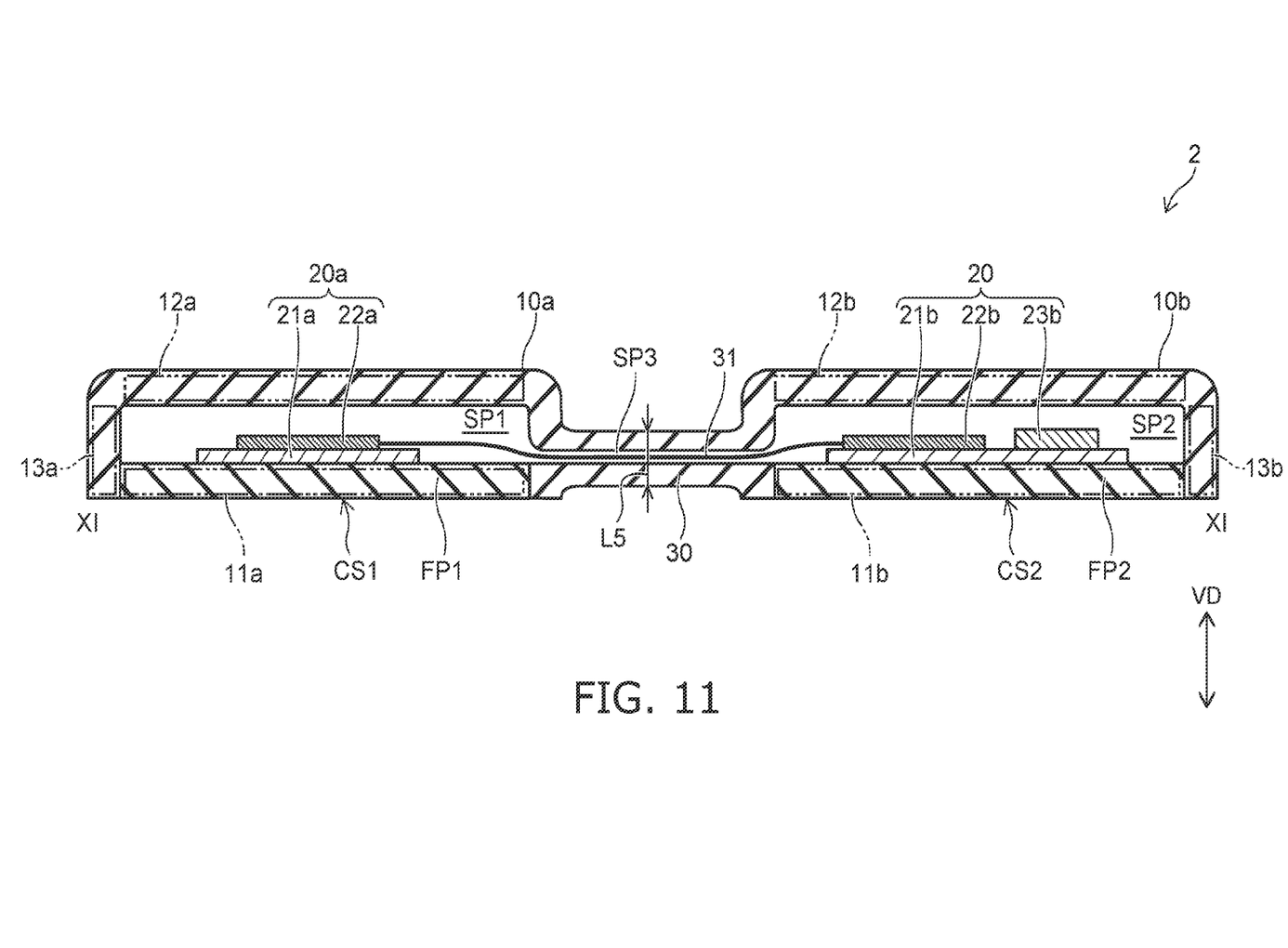
FIG. 11 is a XI-XI cross-sectional view of FIG. 10.

FIG. 11 is a XI-XI cross-sectional view of FIG. 10.

The electronic device 2 according to the modification includes a first housing 10a, a second housing 10b, a first electronic component 20a, a second electronic component 20b, and a coupler 30. The structures of the first and second housings 10a and 10b are similar to the structure of the housing 10 of the electronic device 1.

The first housing 10a includes a first lower surface part 11a, a first upper surface part 12a, and a first side surface part 13a. The first lower surface part 11a and the first upper surface part 12a are separated from each other in the vertical direction VD. The end portion in the vertical direction VD of the first side surface part 13a is connected to the first lower surface part 11a and the first upper surface part 12a. The first housing 10a includes the first space SP1 surrounded with the first lower surface part 11a, the first upper surface part 12a, and the first side surface part 13a.

Similarly, the second housing 10b includes a second lower surface part 11b, a second upper surface part 12b, and a second side surface part 13b. The second lower surface part 11b and the second upper surface part 12b are separated from each other in the vertical direction VD. The end portion in the vertical direction VD of the second side surface part 13b is connected to the second lower surface part 11b and the second upper surface part 12b. The second housing 10b includes a second space SP2 surrounded with the second lower surface part 11b, the second upper surface part 12b, and the second side surface part 13b.

The first electronic component 20a is provided inside the first space SP1. The first electronic component 20a includes, for example, a substrate 21a, and a chip 22a mounted to the substrate 21a. The second electronic component 20b is provided inside the second space SP2. The second electronic component 20b includes a substrate 21b, and a chip 22band a battery 23b that are mounted to the substrate 21b.

The coupler 30 is connected to the first and second housings 10a and 10b. The coupler 30 is tubular. A third space SP3 is formed inside the coupler 30. The third space SP3 communicates with the first and second spaces SP1 and SP2. For example, wiring 31 is provided inside the third space SP3. The wiring 31 is electrically connected to the first electronic component 20a and the second electronic component 20b.

The first lower surface part 11a and the second lower surface part 11b include the contact surfaces CS1 and CS2 that contact the adherend. At least a portion of the first lower surface part 11a and at least a portion of the second lower surface part 11b include the second material. The configuration of the lower surface part 11 of the housing 10 of the electronic device 1 is applicable to the configurations of the first and second lower surface parts 11a and 11b.

For example, the first lower surface part 11a includes the soft part FP1 that is made of the second material. The first lower surface part 11a is bonded to the first side surface part 13. The second lower surface part 11b includes a soft part FP2 that is made of the second material. The second lower surface part 11b is bonded to the second side surface part 13b.

The first upper surface part 12a, the second upper surface part 12b, the first side surface part 13a, and the second side surface part 13b include the second material. The configuration of the upper surface part 12 of the housing 10 of the electronic device 1 is applicable to the configurations of the first and second upper surface parts 12a and 12b. The configuration of the side surface part 13 of the housing 10 of the electronic device 1 is applicable to the configurations of the first and second side surface parts 13a and 13b.

A length L5 in the vertical direction VD of the coupler 30 (illustrated in FIG. 11) is less than the length L1 in the vertical direction VD of the first housing 10a and less than a length L3 in the vertical direction VD of the second housing 10b. A length L6 of the coupler 30 in a direction perpendicular to a direction connecting the first housing 10a and the second housing 10b is less than the length L2 in this direction of the first housing 10a and less than a length L4 in this direction of the second housing 10b.

The coupler 30 includes, for example, the first material. The coupler 30 may be formed from the first material and may be formed to be a continuous body with the first side surface part 13a of the first housing 10a and the second side surface part 13b of the second housing 10b.

For example, the wiring 31 is provided in the coupler 30, and an electronic component is not provided in the coupler 30. Therefore, the coupler 30 can deform more than the first housing 10a and the second housing 10b. For example, when the electronic device 2 is adhered to a surface having a large curve, etc., the contact surfaces CS1 and CS2 can be more widely adhered to the adherend by causing the coupler 30 to greatly curve. Thereby, it is more difficult for the electronic device 2 to peel off from the adherend. For example, compared to when the first electronic component 20a and the second electronic component 20b are provided in one large housing, the contact area of the contact surfaces CS1 and CS2 to the adherend can be larger.

Here, an example is described in which two housings are coupled by one coupler. Specific structures of the electronic device according to the modification are not limited to the example. For example, the electronic device 2 may include three or more housings and multiple couplers that couple the housings to each other.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the invention. The above embodiments can be practiced in combination with each other.

What is claimed is:

1. A housing, comprising:
a lower surface part including a contact surface contacting an adherend;
an upper surface part separated in a vertical direction from the lower surface part with a first space interposed;
a side surface part provided around the first space and connected to the upper surface part and the lower surface part,
the upper surface part and the side surface part including a first material,
the lower surface part including a second material,
the second material being a resin material that is softer than the first material,
a portion of the lower surface part that includes the second material being exposed for at least a portion of the contact surface.

2. The housing according to claim 1, wherein
the lower surface part is formed of the second material and is bonded to the side surface part.

3. The housing according to claim 2, wherein
at least a portion of the lower surface part overlaps the side surface part in a direction perpendicular to the vertical direction.

4. The housing according to claim 2, wherein
one edge of a bonding surface between the lower surface part and the side surface part is positioned at the contact surface.

5. The housing according to claim 1, wherein
the first material includes a resin material, and
a crosslink density of the second material is less than a crosslink density of the first resin material.

6. The housing according to claim 1, wherein
the first material includes at least one of silicone, urethane, epoxy, Teflon (registered trademark), polycarbonate, nylon, or acrylic, and
the second material includes at least one of a silicone gel, a urethane gel, or an acrylic gel.

7. An electronic device, comprising:
the housing according to claim 1;
an electronic component provided inside the first space.

8. A housing, comprising:
a first housing structure including
 a first lower surface part including a first contact surface contacting an adherend,
 a first upper surface part separated in a vertical direction from the first lower surface part with a first space interposed, and
 a first side surface part provided around the first space and connected to the first upper surface part and the first lower surface part;
a second housing structure including
 a second lower surface part including a second contact surface contacting the adherend,
 a second upper surface part separated in the vertical direction from the second lower surface part with a second space interposed, and
 a second side surface part provided around the second space and connected to the second upper surface part and the second lower surface part; and
a coupler connected to the first housing structure and the second housing structure,
the first space and the second space communicating with each other in a third space inside the coupler.

9. The housing according to claim 8, wherein
the first upper surface part, the first side surface part, the second upper surface part, and the second side surface part include a first material,
the first lower surface part and the second lower surface part include a second material, and
the second material is a resin material that is softer than the first material.

10. The housing according to claim 9, wherein
the first material includes a resin material, and
a crosslink density of the second material is less than a crosslink density of the first resin material.

11. An electronic device, comprising:
the housing according to claim 8;
a first electronic component provided inside the first space; and
a second electronic component provided inside the second space.

12. The electronic device according to claim 11, wherein
wiring is provided in the third space of the coupler and connects the first electronic component and the second electronic component.

13. A method for manufacturing a housing, the method comprising:
bonding a second member to a second housing part of a first member to define a first space surrounded with the first and second members, the first member including a first housing part and the second housing part, the second housing part being connected to an outer perimeter of the first housing part, the first member including a first material, the second member including a second material that is softer than the first material.

14. The method for manufacturing the housing according to claim 13, wherein
the first material includes a first resin material, and
the second material is a resin material having a lower crosslink density than the first resin material.

15. A method for manufacturing an electronic device, the method comprising:
bonding a second member to a second housing part of a first member in a state in which a device is provided in a first space surrounded with the first and second members, the first member including a first housing part and the second housing part, the second housing part being connected to an outer perimeter of the first housing part, the first member including a first material, the second member including a second material that is softer than the first material.

16. The method for manufacturing the electronic device according to claim 15, wherein
the first material includes a first resin material, and
the second material is a resin material having a lower crosslink density than the first resin material.

* * * * *